United States Patent [19]

Sieber et al.

[11] Patent Number: 5,039,483
[45] Date of Patent: Aug. 13, 1991

[54] ANTIPROTOZOAN METHOD
[75] Inventors: Fritz Sieber, Brookfield; Orla M. Smith, Milwaukee, both of Wis.
[73] Assignee: The Medical College of Wisconsin, Inc., Milwaukee, Wis.
[21] Appl. No.: 477,285
[22] Filed: Feb. 8, 1990

Related U.S. Application Data

[63] Continuation-in-part of Ser. No. 24,150, Mar. 10, 1987, Pat. No. 4,915,683.
[51] Int. Cl.$^5$ .............................. A61L 2/18; A61J 1/20; A61K 35/14
[52] U.S. Cl. ......................................... 422/28; 422/35; 422/102; 422/292; 422/294; 435/2; 530/412
[58] Field of Search .................... 422/28, 35, 292, 294, 422/102; 435/2; 530/412; 424/529

[56] References Cited

U.S. PATENT DOCUMENTS

| | | | |
|---|---|---|---|
| 3,110,308 | 11/1963 | Bellamy, Jr. | 128/214 |
| 3,140,716 | 7/1964 | Harrison et al. | 128/399 |
| 4,321,919 | 3/1982 | Edelson | 128/214 R |
| 4,398,906 | 8/1983 | Edelson | 604/6 |
| 4,424,201 | 1/1984 | Valinsky et al. | 424/3 |
| 4,428,744 | 1/1984 | Edelson | 604/6 |
| 4,464,166 | 8/1984 | Edelson | 604/6 |
| 4,568,328 | 2/1986 | King | 604/6 |
| 4,573,960 | 3/1986 | Goss | 604/6 |
| 4,573,961 | 3/1986 | King | 604/6 |
| 4,573,962 | 3/1986 | Troutner | 604/6 |
| 4,578,056 | 3/1986 | King et al. | 604/6 |
| 4,596,547 | 6/1986 | Troutner | 604/4 |
| 4,623,328 | 11/1986 | Hartranft | 604/4 |
| 4,727,027 | 2/1988 | Wiesehahn et al. | 435/173 |
| 4,775,625 | 10/1988 | Sieber | 424/3 X |
| 4,846,788 | 7/1989 | Heitz et al. | 514/454 X |
| 4,915,683 | 4/1990 | Sieber | 514/274 X |

FOREIGN PATENT DOCUMENTS 0196515 10/1986 European Pat. Off. .

OTHER PUBLICATIONS

*Journal of Cellular Physiology*, 116: 118-124 (1983), "Susceptibility to Merocyanine 540-Mediated Photosensitization: A Differentiation Marker on Murine Hematopoietic Progenitor Cells," Richard C. Meagher, Fritz Sieber, and Jerry L. Spivak.
*Proc. Natl. Acad. Sci. U.S.A.*, vol. 81, pp. 7584-7587, Dec. 1984, Medical Sciences, "Selective killing of leukemic cells by merocyanine 540-mediated photosensitization," Fritz Sieber, Jerry L. Spivak, and Alison M. Sutcliffe.
*Molecular Basis of Cancer, Part B: Macromolecular Recognition, Chemotherapy, and Immunology*, pp. 227-234, 1985, Alan R. Liss, Inc., "Merocyanine 540-Mediated Photosensitization of Leukemia and Solid Tumor Cells," Fritz Sieber.
*Cancer Research* 46, pp. 2072-2076, Apr. 1986, "Dye-mediated Photosensitization of Murine Neuroblastoma Cells," Fritz Sieber and Maya Sieber-Blum.
*Blood*, vol. 68, No. 1 (Jul.) 1986, pp. 32-36, "Dye-Mediated Photolysis of Human Neuroblastoma Cells: Implications for Autologous Bone Marrow Transplantation," Fritz Sieber, Sanjay Rao, Scott D. Rowley, and Maya Sieber-Blum.
*Minimal Residual Disease in Acute Leukemia*, 1986, A. Hagenbeek, B. Lowenberg (editors), Martinus Nijhoff Publishers, "Detection and Selective Destruction of Tumor Cells by the Lipophilic Dye, Merocyanine 540", pp. 282-294, Fritz Sieber.
*Transfusion*, vol. 26, No. 5, 1986, pp. 481-483, "*Inactivation of Human T-Cell Lymphotropic Virus, Type III by Heat, Chemicals, and Irradiation,*" Gerald V. Quinnan, Jr., Martha A. Wells, Alec E. Wittek, Michael A. Phelan, Ronald E. Mayner, Stephen Feinstone, Robert H. Purcell and Jay S. Epstein.
Sieber et al. Abstract "Antiviral Activity of Merocyanine 540," dated Feb. 15-19, 1987.

*Primary Examiner*—Jill Johnston
*Attorney, Agent, or Firm*—Quarles & Brady

[57] ABSTRACT

A method of treating a body fluid so as to inactivate protozoa in said fluid comprises mixing the body fluid with an effective amount of a photosensitizing agent which will bind to cell-free protozoa and/or protozoan-infected cells, and then exposing the resulting mixture to visible light to inactivate the protozoa. An apparatus for use in the method includes at least one container which contains a body fluid containing protozoa and an effective amount of a photosensitizing agent to bind to the protozoa. The apparatus has at least one wall which is permeable to visible light.

6 Claims, 1 Drawing Sheet

ANTIPROTOZOAN METHOD

RELATED CASES

This application is a continuation-in-part of patent application U.S. Ser. No. 24,150 filed Mar. 10, 1987 now U.S. Pat. No. 4,915,683.

FIELD OF THE INVENTION

The present invention relates to the field of medicine. More particularly, it relates to a method of inactivating protozoa in body fluids, especially blood and blood products, and agents and apparatus for use in that method.

BACKGROUND OF THE INVENTION

The protozoan parasite, *Plasmodium falciparum*, causes the fatal form of human malaria and it is responsible for over one million deaths among African children annually. Although normally transmitted by the bite of a mosquito vector, malaria can also be transmitted through the transfusion of blood from asymptomatic donors.

It would be useful to have a method of inactivating protozoa, such as *Plasmodium falciparum*, in whole blood and cellular blood products, such as red cells (Chojnacki et al., New Engl. J. Med.279: 984-985, 1968 and Grant et al., Lancet II 469-491, 1960).

BRIEF SUMMARY OF THE INVENTION

It is an object of the present invention to disclose a method of inactivating protozoa in body fluids.

It is a further object to disclose an apparatus for use in the method.

It is a still further object to disclose photosensitizing agents for use in the method.

Other objects and advantages will be apparent from the description which follows.

We have now discovered that certain protozoa in body fluids, including blood and red blood cells, can be inactivated by contacting the fluids with an effective amount of a photosensitizing agent which binds to the protozoa or protozoan-infected cells and exposing the resulting mixture to visible light until the protozoa and/or protozoan-infected cells have been inactivated. The treated body fluids are then safe for infusion into a patient.

For the treatment of blood or red blood cells, the method of the invention offers the following advantages:

1. It is selective. It inactivates cell-free protozoa and protozoan-infected cells. It is, however, much less toxic to non-infected red cells, leukocytes, pluripotent hematopoietic stem cells and plasma/serum components (e.g. coagulation proteins).

2. It may be effective against protozoa for which routine screening procedures do not yet exist.

3. It does not restrict the available pool of blood donors.

4. It is relatively non-toxic and excess photosensitizing agent or dye can be easily removed.

5. It uses visible light.

The photosensitizing agents which are to be used in the method of the present invention are agents which preferentially bind to the cell-free protozoa in the blood or protozoan-infected red blood cells and which do not or bind only minimally to normal blood components. The agents which are preferred for use in the method are merocyanine dyes which do not bind to the DNA and are probably non-mutagenic and which have been used in the past as fluorescent probes to study the structure and function of biological membranes (Cohen et al. J. Membr. Biol., 19, 1-36 (1974)). The merocyanine dyes, have been shown to undergo transient, voltage-dependent fluorescence enhancements in response to electrical stimulation when they are incorporated into excitable membranes (Davila et al., Nature New Biol., 241, 159-160 (1973)). The generation of electrochemical potentials in human (Sims et al., Biochemistry, 13 3315-3330 (1974)) and Amphiuma red cell membranes (Hoffman and Laris, J. Physiol, 239. 519-552 (1974)), enhances the fluorescence of some of these dyes. These probes have been successfully used in the detection of leukemic cells, Valinsky et al., U.S. Pat. No. 4,424,201, and more recently for the selective killing of leukemic cells in bone marrow by agent-mediated photosensitization (Sieber et al., Proc. Natl. Acad. Sci. U.S.A. Vol 81, pp. 7584-7587 December 1984).

The preferred agents are compounds of the formula

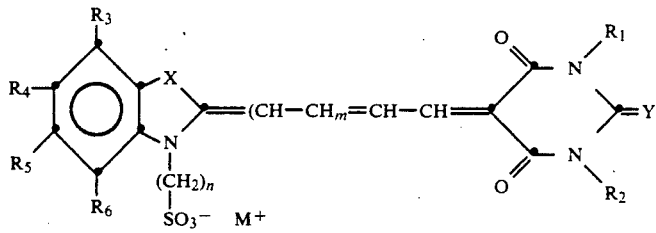

wherein n is 1-5; m is 1 to 4; X is oxygen (O), sulfur (S), $-CR_1R_2-$, or selenium (Se); Y is O, S or Se; M is an alkaline metal or other basic group; $R_1$ and $R_2$ are the same or different alkyl groups of 1 to 8 carbons; and $R_3$, $R_4$, $R_5$, and $R_6$ are selected from hydrogen, lower alkyl groups of 1 to 5 carbons, lower alkoxy groups of 1 to 5 carbons, phenyl lower alkyls, such as phenylmethyl; or $R_3$ and $R_4$, or $R_4$ and $R_5$, or $R_5$ and $R_6$ are part of an aromatic ring.

The method of the invention may be practiced on a continuous basis using a known apparatus, such as disclosed in Edelson U.S. Pat. No. 4,321,919, which is incorporated by reference herein, or on a batch basis using the novel apparatus of the present invention.

The novel apparatus of the present invention is particularly adapted for the collection, handling, treatment of a sample of a body fluid, especially blood and blood products, with the photosensitizing agent and light and storage of sample until time of use. The preferred apparatus comprises at least one inert, biocompatible, sterile container permeable to visible light which contains an effective amount of the photosensitizing agent to inactivate the protozoa in the body fluid to be collected when the container and its contents are exposed to visible light. The container may be connected to other containers to form a closed system. Preferably the container is of a disposable transparent plastic, such as polyvinyl chloride resin, which has been used in the collection and handling of blood. The preferred apparatus also includes a length of collection tubing attached at one end to the container and having at the other end a needle or catheter for collecting blood or another body fluid.

The light source for use with the method of the present invention includes any light source that will provide visible light of a suitable wavelength for the desired length of time. Especially preferred is the light source of the photopheresis system available from the THERAKOS Division of Johnson and Johnson Cardiovascular of King of Prussia, Pa. under the trade name UVAR.

The exact mechanism of inactivation of protozoa by the method of the present invention is not yet fully understood. However, it is known that malarially-infected human and duckling erythrocytes are stained more intensely by merocyanine 540 than other noninfected cells. (Sherman and Greenan, Trans. Roy. Soc. Trop. Med. Hyg 78: 641-644, 1984). The photoexcitation of the photosensitizing agent molecules appears to lead to the formation of reactive oxygen species, such as singlet oxygen, which cause peroxidation and inactivation of the protozoa.

Variables which can affect the method are agent concentration, protein concentration, protein composition, geometry and optical properties of the container, intensity and spectral properties of the light source and duration of the illumination. Those skilled in the art will appreciate that each of those variables can be varied within rather wide margins, provided the other variables are adjusted accordingly.

DESCRIPTION OF THE PREFERRED EMBODIMENT

Figure 1:
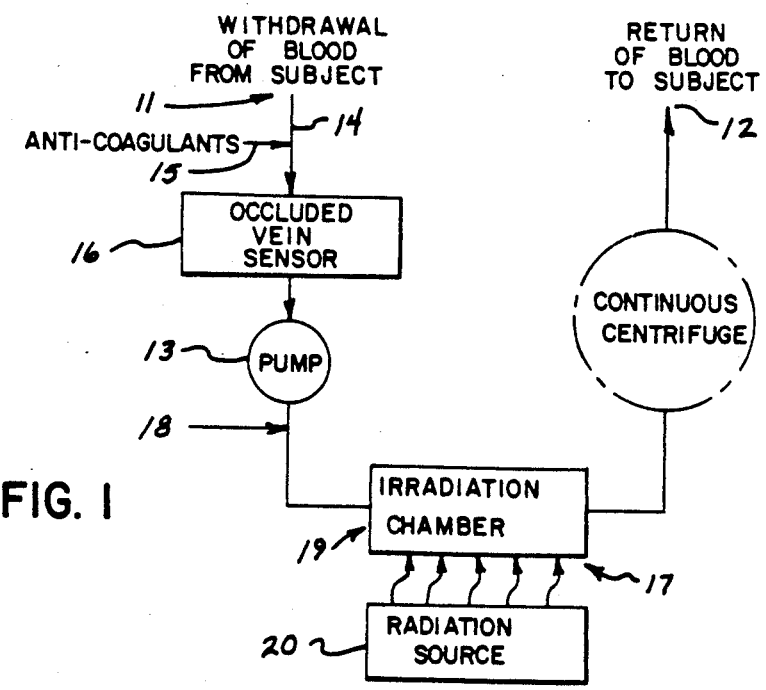
FIG. 1 is a schematic flow diagram illustrating a preferred embodiment of a system operating in accordance with the present invention.

In FIG. 1 herein a schematic diagram is shown of a system 10 for use with the method of the present invention. It is the system of U.S. Pat. No. 4,321,919, supra.

As shown schematically in FIG. 1, blood may initially be withdrawn from the human subject, as at 11. Typically the blood is withdrawn via a donor needle, which may be placed in the right antecubital vein. In the system 10 of FIG. 1, it is assumed that the processing of blood is conducted on a continuous basis from 11 to a final return of the blood to the subject at 12. The return at 12 is via a recipient needle positioned in the left antecubital vein. Where the method is continuous a typical blood flow is in range of from about 10 to 75 ml/min. with a preferred range being from about 40 to 50 ml/min. The desired flow rates are produced by a pump 13, which is positioned in the extracorporeal blood flow stream generally indicated as 14.

Anti-coagulants are preferably injected into the extracorporeal blood flow stream at 15, close to the point of blood withdrawal. Such anti-coagulants can comprise solutions of acid, citrate and dextrose and/or heparin, or of other known anti-coagulant compositions. An occluded vein sensor 16 is preferably provided in stream 14 to prevent or inhibit the generation or continued existence of bubbles in the blood flow stream.

In the preferred mode of practicing the continuous mode of the method of the present invention, the photosensitizing agent is added to the blood after it leaves the human. Thus, as shown in the system 10 of FIG. 1, the agent may be added to the flowing blood downstream of pump 13, and just upstream of where the blood enters the irradiation station 17.

The photosensitizing agent is usually first dissolved in an isotonic solution, which thereafter is directly injected into the flowing blood stream, as at 18. The agent is injected at a rate which takes into account the blood flow rate and achieves a concentration of the agent in the blood in the desired range as the blood passes through the irradiation station 17.

It will be appreciated that the photosensitizing agent may not need to be directly introduced by injection into the extracorporeal blood stream 14. It also might be possible to obtain the desired concentration of the agent by orally or otherwise administering the compound directly to the patient. Alternate modes of administration of the photosensitizing agents are within the scope of this invention and the doses appropriate therefore will be apparent to those skilled in the art.

The introduction of the photosensitizing agents to the extracorporeal stream is preferred because it makes it possible to achieve more exact concentration levels; and to avoid or minimize possible side effects and the like, which can occur from administration of any drug directly to the body system.

At irradiation station 17, which consists of an irradiation chamber 19 and radiation source 20, the blood containing the desired concentration of dissolved photosensitizing agent, is subjected to visible light and preferably visible light having the bulk of its spectral components in the preferred orange to green range for the activation of the particular photosensitive agent being employed in the treatment being conducted. The irradiation station 19 is constructed so as not to block radiation in the desired portion of the visible light spectrum and to prevent the body fluid from being overheated and damaged.

Figure 2:
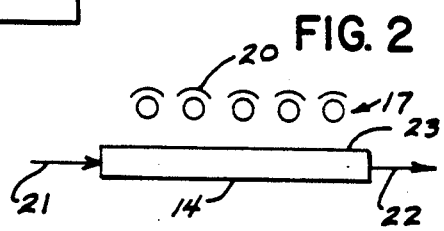
FIG. 2 is a schematic elevational view of the irradiation station portion of the FIG. 1 system.

In FIG. 2, a schematic view appears of an irradiation station 17 of a type suitable for use with the invention. The preferred station 17 consists of a blood treatment or irradiation chamber 19, having an inlet 21 and an outlet 22, enabling blood flow through the chamber, and a spaced source 20 of visible light. The chamber 19 can take various forms, with the principal requirement that it have at least one wall 23 which is substantially transparent to visible light. The chamber (or at least wall 23) therefore can be comprised of various substantially visible light transparent plastics, such as polyvinyl chloride and the like.

In the irradiation chamber 19, the body fluid to be treated flows through a flow passage which is of relatively thin cross-section e.g., about 2 mm thick if the fluid contains a high concentration of red blood cells. The total surface area of the flow passage in the chamber 19 is calculated to provide the blood contained therein with the desired radiation dose level from the visible light source 20. Especially preferred is an apparatus consisting of a plurality of fluorescent tubes with concentric jackets spaced from the tubes to form the flow passages for the body fluid to be irradiated.

The visible light source can comprise commercially available lamps, numerous types of which are known in the art. By way of example, source 20 can comprise a single incandescent or fluorescent lamp or multiple lamps which preferably emit visible light in the orange to green spectrum, i.e., between about 5200 to about 6500 Angstroms, which is preferred when a merocyanine dye of the type described in FIG. 1 is the photosensitizing agent being employed in the method of the invention. With the continuous flow rates utilized in accordance with one aspect of the invention, such a source will provide the desired amount of absorbed energy in the flowing blood for practicing the method of the invention.

The blood flow from irradiation station 17 proceeds as shown in FIG. 1 via outlet 22 back to the subject at 12. Optionally, however, prior to returning the treated blood to the patient, it may be heat exchanged so as to adjust its temperature to that of the patient's circulating blood. Heat exchange may be necessary whenever the treated blood, by consequences of its treatment, has attained a temperature substantially at variance with that of the patient.

Regardless of which photosensitizing agent is employed in the invention or at what rate it is administered the burden placed upon the body's organ system can be further alleviated, by utilizing in conjunction with the present system, a continuous centrifuge (or other filtration system), which device can be used to separate photosensitizing agents.

Figure 3:
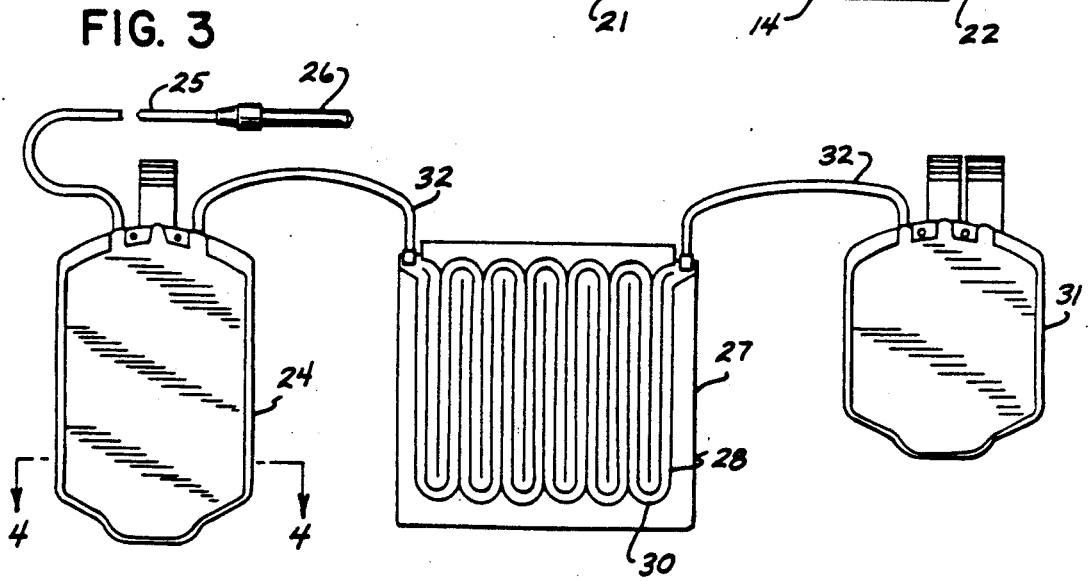
FIG. 3 is a perspective view of a preferred embodiment of an apparatus of the present invention.
Figure 4:
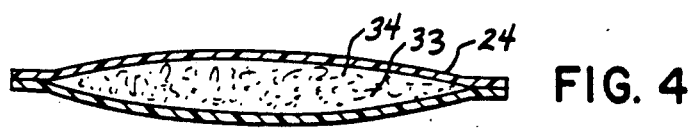
FIG. 4 is a cross sectional view taken along lines 4—4 of FIG. 3.

The preferred embodiment of the apparatus of the invention which is used when whole blood is collected, treated to inactivate protozoa and stored to be later administered to the donor or another human is shown in FIGS. 3 and 4. The apparatus as seen in FIG. 3 comprises a first container 24, which is provided with collection tubing 25 and a needle 26; an irradiation chamber 27 comprising a flat, plastic envelope 28 with a continuous flow passage 30; a storage container 31; and tubing 32 which connects the first container 24, the irradiation chamber 27 and the storage container 31 into a closed system. The body fluid can be transferred from the container 24 to the irradiation chamber 27 where it is exposed to visible light and maintained at a safe temperature e.g., by a water bath. It is then transferred to the storage container 30. The body fluid can be transferred through the system by squeezing the first container 24 and/or by use of a tubing pump (not shown). Alternatively, the novel apparatus may take the form of a single container, containing the photosensitizing agent, in which the body fluid can be collected, treated with visible light and stored.

In the apparatus of FIG. 3, an effective amount of anticoagulant liquid 33 containing the photosensitizing agent represented by dots 34 is already in the first container 24. Of course, the agent 34 may be added to the apparatus at any time prior to treatment of the blood or blood products with the visible light. The apparatus and its contents are preferably agitated to bring the agent into contact with the protozoa in the body fluids before treating the mixture with visible light to inactivate the protozoa. If the body fluid is blood it can then be divided into its various components either before or after addition of the photosensitizing agent and/or exposure to visible light. Any excess photosensitizing agent can, if desired, be removed any time after the light exposure by conventional means.

In those embodiments of the inventions in which the product containing the protozoa to be inactivated is not blood collected directly from a donor, the photosensitizing agent may be added to the product immediately prior to light exposure. For example, when the product is blood cells they are first suspended in a physiological medium and when the product is bone marrow or blood cells, it is preferred to suspend it in deuterium oxide ($D_2O$) because the presence of $D_2O$ shortens the illumination time required, presumably by extending the half life of singlet oxygen. The photosensitizing agent is then added to the solution or suspension and the resulting mixture stirred or otherwise agitated to bring the agent into contact with the protozoa or protozoan-infected cells. The mixture is then exposed to visible light of a suitable wavelength. In an aqueous environment the preferred excitation spectrum peaks for MC 540 are at 510 and 535 nm and in an organic phase, the spectrum is redshifted to 565 nm. Structural analogs may have somewhat different absorption characteristics. After completion of the photosensitization step the excess agent may be separated from the desired blood component by centrifugation, precipitation with solvents or salt, solvent extraction, or by chromatographic or other means. If desired, undesired components such as plasma proteins, can be separated from the mixture by precipitation with solvents or salt, solvent extractions, or by chromatographic means.

Representative of the specific agents that can be used are the following:

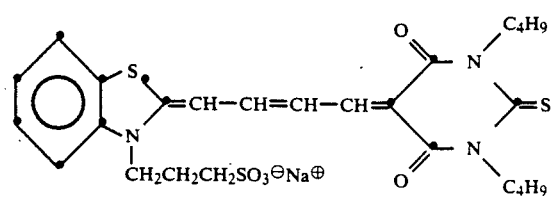

-continued

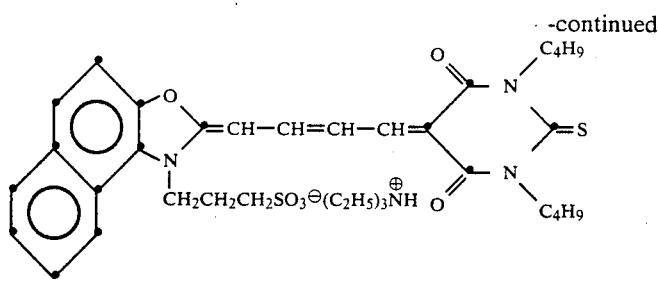

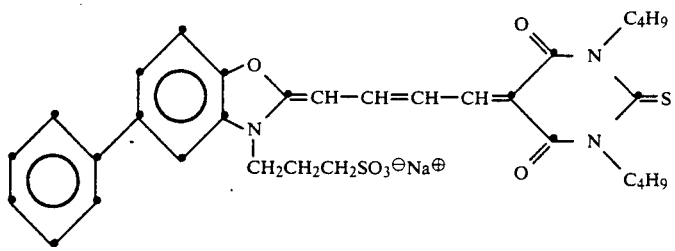

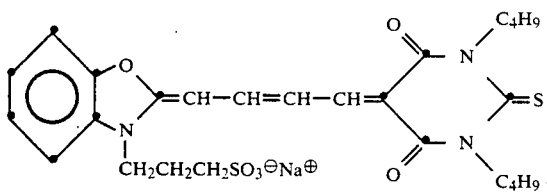

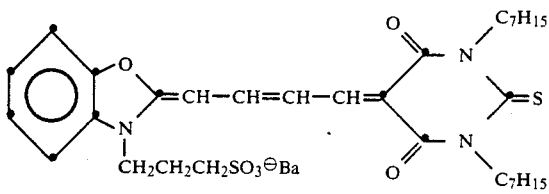

The photosensitizing agent is employed in an amount which is effective under the conditions of use to accomplish the inactivation of the protozoa which may be present. Some of the agents, of course, are more active than others and can be used in smaller amounts. The toxicity of the preferred merocyanine dyes is very low. Therefore, it is not essential that they be completely removed from the treated body fluid, blood, blood product or bone marrow before administration to a patient.

The merocyanine, MC 540, is normally used with light of suitable wavelength in an amount of about 10 micrograms to about 25 micrograms per milliliter of body fluid and a more active merocyanine derivative, MC 540A, is used in an amount of about 5 micrograms to about 10 micrograms per milliliter under comparable conditions.

The effective wavelengths of visible light that can be used vary and depend on the absorption characteristics of the chosen dye, it is generally desired that the light be of a wavelength in the green to orange range when the agent is a merocyanine dye. It appears that blue light and dark red light is not effective with the preferred merocyanine dyes.

Tests have shown that:

1) Seventy to one hundred percent of mice receiving malarious (P. yoelii) blood which had been treated for 60 minutes with the photosensitizing agent and light survived. In contrast one hundred percent of the mice receiving untreated malarious blood died.

2) The same treatment protocol was much less toxic to mature blood cells and normal pluripotent hematopoietic stem cells in the mouse.

3) Photosensitized plasma clots normally, suggesting that at least some clotting factors are still intact.

4) The small amounts of dye that are transferred with photosensitized red blood cells do not appear be to toxic to mice.

The simultaneous exposure to MC 540 and visible light appears to kill protozoan-infected red blood cells very rapidly, but normal pluripotent hematopoietic stem cells and mature blood cells very slowly. This differential sensitivity to MC 540-mediated photolysis may be useful in purging blood and red blood cells of cell-free protozoa and protozoan-infected cells thus making the blood supply safer for use.

An analog of MC 540 which we have labeled MC 540A (see structural formula below) may be helpful in reducing illumination times when used in equimolar concentrations.

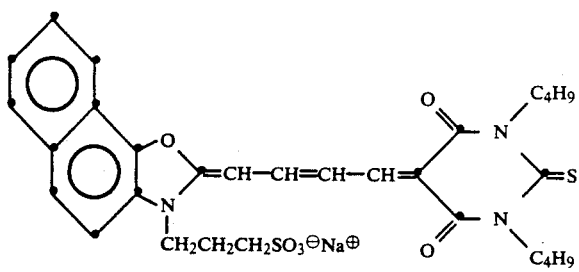

Merocyanine-mediated photolysis of tumor cells and viruses appears to be primarily mediated by singlet oxygen and an additional 2-fold reduction in illumination time can therefore be achieved by performing the photosensitization step in the presence of deuterium oxide ($D_2O$). The same technique may be useful for inactivating protozoa.

Unlike heat, high doses of ionizing radiation, solvents, or detergents, MC 540-mediated photolysis is more selective in its toxicity. Most mature leukocytes and primitive hematopoietic progenitor cells are highly resistant to MC 540-mediated photolysis and the ability of plasma to clot is not significantly impaired. Dye-mediated photosensitization may be the preferred antiprotozoan treatment in situations where critical components are temperature or radiation sensitive. The acute systemic toxicity of merocyanines is low. The amount of dye that is injected with a typical mouse bone marrow graft is more than 100,000 times less than the $LD_{10}$ in the same species.

The invention is further illustrated by the following examples.

EXAMPLE 1

Using the rodent malaria species, *P. yoelii* YM, and *P. berghei berghei* as model systems, the survival of mice i.v. injected with MC 540-treated and non-treated malarious blood was monitored in vivo. Treatment of *P. yoelli*-infected blood (40%-70% parasitemia) with dye and light for 90 minutes resulted in total protection of the recipient mouse population while 60 minutes of dye/light treatment resulted in survival of 70%-100% of the recipient population. Shorter illumination times provided partial protection. All mice receiving untreated malarious blood died rapidly. In a subsequent experiment, serial dilutions of treated (30 minutes of dye/light) or control malarious blood (30% parasitemia) were injected into recipient mice. One hundred percent of the mice receiving $10^4$ treated cells survived compared to 0% of the corresponding control group. It was observed in both treatments that some of the surviving mice initially showed severe symptoms of malaria (e.g. splenomegaly, anemia) but later recovered. It is conceivable that MC 540 treatment of infected blood enhanced the immune response of the recipient mice.

In two experiments, all mice receiving *P. berghei*-infected blood (30% parasitemia), treated for 15-45 minutes with light and MC 540, died as did their control counterparts. However, 10% of the group receiving infected blood treated for 60 minutes with light and dye survived for the duration of the experiment (90 days).

*P. yoelii* preferentially infects mature erythrocytes while *P. berghei* prefers to invade reticulocytes. The enhanced killing of *P. yoelli*-infected cells compared to *P. berghei*-infected cells may reflect a greater susceptibility of erythrocytes (compared to reticulocytes) to MC 540-mediated photoinactivation. *P. falciparum* invades erythroid cells at all of the later stages of development. However, only 2 of the 4 parasite developmental stages of *P. falciparum* are found in the peripheral blood and these are at such a low cell density in asymptomatic carriers as to be undetectable in thick or thin smears. In our in vivo experiments, *P. yoelii*-infected blood with exceedingly high parasitemias representing all stages of development was used and protection by MC 540 treatment was still obtained.

EXAMPLE 2

The acute systemic toxicity of MC 540 was determined by injecting groups of 10 BAF1 mice intravenously with graded doses of MC 540. Survival data were plotted on a log probit scale and fitted with a least square regression line to determine $LD_{10}$ and $LD_{50}$ (Table 1). It should be pointed out that MC 540 is not more toxic than the fluorescent dyes that are commonly used for the angiography of the retina. Necropsies showed that the probable cause of death after high doses of MC 540 was the formation of large emboli of precipitated dye in major blood vessel (i.e., we killed the mice by exceeding the solubility of the dye in plasma).

TABLE 1

| Acute Toxicity of MC 540 | |
|---|---|
| $LD_{10}$ (mouse) | 55 mg/kg |
| $LD_{50}$ (mouse) | 84 mg/kg |
| Injected with photosensitized marrow graft | 0.0004 mg/kg |
| For comparison | |
| $LD_{50}$ (mouse) fluorescein | 300 mg/kg |
| $LD_{50}$ (mouse) indocyanine green | 70 mg/kg |

MC 540-sensitized photoirradiation (or photoirradiation sensitized by structural analogs of MC 540) may prove useful as a means of inactivating malarially-infected cells in blood or blood products. In addition, one may speculate that this technique could prove useful for purging other blood-borne protozoan parasites, such as *Trypanosoma cruzi*, the causative organism of Chaga's disease, from the donor blood supply.

It will be readily understood by those skilled in the art that the foregoing description has been for purposes of illustration only and that a number of changes may be made without departing from the scope of the invention. For example, the containers of the novel apparatus may take a wide variety of shapes and forms. In addition to being shaped like conventional blood bags, they can also be elongated tubes or other shapes. Further, the agent need not be physically in the containers as long as it can be added thereto before or after the addition of the body fluid, preferably without opening the system to the outside. Therefore, it is intended that the invention not be limited except by the claims.

References

Chojnacki R. E., Brazinsky J. H., Barrett O.: Transfusion-introduced *Falciparum malaria*. New Engl J Med 279: 984–985, 1968.

Cohen, L. B., Salzberg, B. M., Davila, H. V., Ross, W. N., Landowne, D., Waggoner, A. S. and Wang, C. H.: Changes in axon fluorescence during activity: molecular probes of membrane potential. J. Membr. Biol. 19:1–36, 1974.

Davila, H. V., Salzberg, B. M. and Cohen, L. B.: A large change in axon fluorescence that provides a promising method for measuring membrane potential. Nature (New Biology) 241:159-160, 1973.

Grant D. B., Perinpanayagam M. S., Shute P. G., Zeitlin R. A.: A case of malignant tertian (*Plasmodium falciparum*) malaria after blood-transfusion. Lancet ii: 469-491, 1960.

Hoffman, J. F. and Laris, P. C.: Determination of membrane potentials in human and Amphiuma red blood cells by means of a fluorescent Probe. J. Physiol. 239:519-552, 1974.

Sherman I. W., Greenan J. R. T.: Altered red cell membrane fluidity during schizogonic development of malarial parasites (*Plasmodium falciparum* and *P. lophurae*). Trans Roy Soc Trop Med Hyg 78: 641-644, 1984.

Sieber, F., Spivak, J. L. and Sutcliff, A. M.: Selective killing of leukemic cells by merocyanine 540-mediated photosensitization. Proc. Natl. Acad. Sci. USA 81:7584-7587, 1984.

Sims, P. J., Waggoner, A. S., Wang, C-H. and Hoffman, J. F.: Studies on the mechanism by which cyanine dyes measure membrane potential in red blood cells and phosphatidylcholine vesicles. Biochemistry 13:33153330, 1974.

We claim:

1. A method of in vitro treating blood and cellular blood products from an animal to inactivate protozoa therein which comprises first bringing said blood and cellular blood products into contact with an effective amount of a photosensitizing agent which selectively binds to cell-free protozoa and protozoan-infected cells in a container and then exposing the combination of the blood and cellular blood products and agent to visible light to photosensitize and inactivate the protozoa so that said blood and cellular blood products can be returned to an animal, said photosensitizing agent having the following formula:

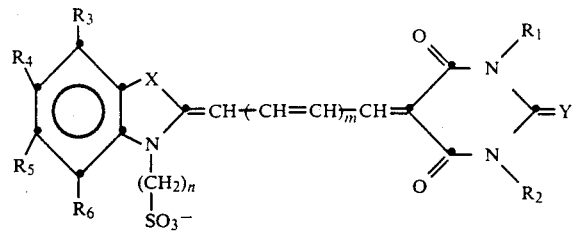

in which n is 1-5, m is 1 to 4, x is oxygen (O), sulfur (S), $-CR_1R_2-$ or selenium (Se); Y is O, S or Se, M is alkaline metal or other basic group $R_1$ and $R_2$ are the same or different alkyl groups of 1 to 8 carbon; and $R_3$; $R_4$, $R_5$ and $R_6$ are selected from hydrogen, lower alkyl groups of 1 to 5 carbons, lower alkoxy groups of 1 to 5 carbon atoms, phenyl lower alkyls; or $R_3$ and $R_4$, or $R_4$ and $R_5$, or $R_5$ and $R_6$ are part of an aromatic ring.

2. The method of the claim 1 in which the photosensitizing agent is merocyanine 540.

3. An apparatus for the photosensitization of blood and cellular blood products to inactivate protozoa in the blood or cellular blood products, said apparatus comprising at least one inert, biocompatible container containing the blood or cellular blood products and an effective amount of a photosensitizing agent of claim 1 to bind with protozoa to affect the inactivation of protozoa in the presence of visible light, said container having a wall portion which is permeable to visible light.

4. An apparatus of claim 3 in which the container is of a flexible plastic.

5. An apparatus of claim 3 in which the photosensitizing agent is selected from merocyanine 540 and its structural analogs.

6. An apparatus of claim 3 in which the container is connected by tubing to an irradiation chamber to form a closed system.

* * * * *

UNITED STATES PATENT AND TRADEMARK OFFICE
CERTIFICATE OF CORRECTION

PATENT NO. : 5,039,483

DATED : August 13, 1991

INVENTOR(S) : Sieber et al.

It is certified that error appears in the above-identified patent and that said Letters Patent is hereby corrected as shown below:

Column 1, line 8, please insert the following:

--This invention was made with government support under Federal Grant 5ROI CA-42734-06 awarded by the National Institutes of Health. The government has certain rights in the invention.--

Signed and Sealed this

Thirteenth Day of April, 1993

*Attest:*

STEPHEN G. KUNIN

*Attesting Officer*     *Acting Commissioner of Patents and Trademarks*